(12) United States Patent
Hornung et al.

(10) Patent No.: US 7,188,519 B2
(45) Date of Patent: Mar. 13, 2007

(54) DEVICE AND METHOD FOR MEASURING THE FLOW AND AT LEAST ONE MATERIAL PARAMETER OF A FLUID

(75) Inventors: Mark Hornung, Zürich (CH); Jens Kubasch, Zürich (CH); Moritz Lechner, Zürich (CH); Felix Mayer, Zürich (CH)

(73) Assignee: Sensirion AG, Zürich (CH)

( * ) Notice: Subject to any disclaimer, the term of this patent is extended or adjusted under 35 U.S.C. 154(b) by 244 days.

(21) Appl. No.: 10/690,383

(22) Filed: Oct. 20, 2003

(65) Prior Publication Data

US 2004/0099057 A1    May 27, 2004

(30) Foreign Application Priority Data

Nov. 27, 2002  (CH) .................................... 2001/02

(51) Int. Cl.
*G00F 1/68* (2006.01)
(52) U.S. Cl. .................................................. 73/204.26
(58) Field of Classification Search ............. 73/204.26, 73/204.24, 204.11, 202.5; 374/45; 431/20
See application file for complete search history.

(56) References Cited

U.S. PATENT DOCUMENTS

| | | | |
|---|---|---|---|
| 4,373,386 A | 2/1983 | Schuddemat et al. ......... 73/189 |
| 4,501,145 A | 2/1985 | Boegli et al. .................. 73/204 |
| 4,693,116 A * | 9/1987 | Miura et al. ............. 73/204.16 |
| 4,712,996 A * | 12/1987 | Adams et al. ................ 431/20 |
| 4,909,078 A | 3/1990 | Sittler et al. ............. 73/204.26 |
| 5,339,687 A | 8/1994 | Gimson et al. ........... 73/204.19 |
| 5,406,841 A | 4/1995 | Kimura .................... 73/204.26 |
| 5,533,412 A | 7/1996 | Jerman et al. ........... 73/861.95 |
| 5,596,219 A | 1/1997 | Hierold ....................... 257/467 |
| 5,804,720 A | 9/1998 | Morimasa et al. ....... 73/204.26 |
| 5,830,372 A | 11/1998 | Hierold ......................... 216/2 |
| 5,980,102 A * | 11/1999 | Stulen et al. .................. 374/45 |
| 6,209,402 B1 | 4/2001 | Yamada .................... 73/861.26 |
| 6,349,596 B1 | 2/2002 | Nakada et al. ........... 73/204.26 |

(Continued)

FOREIGN PATENT DOCUMENTS

| | | |
|---|---|---|
| DE | 19960538 | 7/2000 |
| DE | 10129300 | 2/2002 |
| EP | 0484645 | 5/1992 |
| EP | 1065475 | 1/2001 |

(Continued)

OTHER PUBLICATIONS

F. Cascetta et al., "The future domestic gas meter: Review of current developments", 8252 Measurement, Apr. 13, 1994, No. 2, pp. 129-145.

(Continued)

Primary Examiner—Jewel V. Thompson
(74) Attorney, Agent, or Firm—Donald S. Dowden; Cooper & Dunham LLP

(57) ABSTRACT

For measuring the flow and the thermal conductivity of a fluid, a sensor is used, which has a first temperature detector for measuring a first temperature and a second temperature detector for measuring a second temperature. A heating is arranged between the temperature detectors. Two measured quantities are determined by means of the temperature detectors, a first of which is e.g. a difference between the temperatures and a second one of which is one of the temperatures. By comparing the two measured quantities, the flow and the thermal conductivity of the fluid can be determined.

18 Claims, 2 Drawing Sheets

U.S. PATENT DOCUMENTS

| | | | |
|---|---|---|---|
| 6,460,411 B1 | 10/2002 | Kersjes et al. | 73/204.26 |
| 6,550,325 B1* | 4/2003 | Inushima et al. | 73/204.26 |
| 6,684,694 B2* | 2/2004 | Fujiwara et al. | 73/204.26 |
| 2003/0115952 A1 | 6/2003 | Mayer et al. | 73/204.26 |

FOREIGN PATENT DOCUMENTS

| | | |
|---|---|---|
| EP | 1094306 | 4/2001 |
| WO | WO 0118500 | 3/2001 |
| WO | WO 0181872 | 11/2001 |
| WO | WO 0198736 | 12/2001 |

OTHER PUBLICATIONS

M. Ashauer et al., "Thermal flow sensor for Liquids and Gases", Proc. IEEE. 98CH36176, pp. 351-355.

F. Mayer et al., "Scaling of Thermal CMOS Gas Flow Microsensors: Experiment and Simulation", Proc. IEEE. 96CH35856, pp. 116-121.

* cited by examiner

DEVICE AND METHOD FOR MEASURING THE FLOW AND AT LEAST ONE MATERIAL PARAMETER OF A FLUID

CROSS REFERENCE TO RELATED APPLICATIONS

This application claims the priority of Swiss patent application 2001/02, filed Nov. 27, 2002, the disclosure of which is incorporated herein by reference in its entirety.

BACKGROUND OF THE INVENTION

The invention relates to a device and method for measuring the flow and at least one material parameter of a fluid, such as a composition of the fluid, as well as an apparatus for mixing fluids.

WO 01/18500 describes a device where the thermal conductivity and the mass flow of a gas are measured. It comprises, on the one hand, a conventional thermal flow sensor with a heater, referred to herein also as a "heating," and two temperature detectors arranged symmetrically thereto, which is arranged in the flowing gas, and, on the other hand, an identically designed reference sensor arranged in a non-flowing section of the gas. Such a device allows a more accurate determination of the flow because the thermal conductivity of the gas can be determined more accurately by means of the reference sensor, which can be used for a correction of the flow value.

BRIEF SUMMARY OF THE INVENTION

It is a general object of the invention to improve this type of device and method, in particular by simplifying device design and/or increasing accuracy.

Now, in order to implement this and still further objects of the invention, which will become more readily apparent as the description proceeds, the device is manifested by the features that it is adapted for measuring the flow m and at least one material parameter k of a fluid, wherein the material parameter k depends on a thermal conductivity of the fluid, wherein the device comprises a heating for generating, in said fluid, a region having non-homogeneous temperature, several sensors for determining at least two measured quantities t1, t2 depending on fluid temperatures in a range of influence of the heating, wherein the measured quantities are different functions $t1=f1(m, k)$ and $t2=f2(m, k)$ of the flow m and the material parameter k, and a processing circuit for determining the flow m and the material parameter k from the measured quantities t1, t2.

In another aspect, the invention is directed to a method for measuring a flow m of a fluid and a material parameter k depending on a composition of the fluid, said method comprising the steps of bringing said fluid into contact with a heating for generating a region having non-homogeneous temperature in said fluid, determining at least two measured quantities t1, t2 depending on fluid temperatures in a range of influence of the heating, wherein the measured quantities are different functions $t1=f1(m, k)$ and $t2=f2(m, k)$ of the flow m and the material parameter k, and determining the flow m and the material parameter k from the measured quantities t1, t2.

This type of technology can be applied to determining a mixing ratio or composition of a fluid. Hence, in a further aspect of the invention, it is an object to provide a means for monitoring and/or controlling mixed fluids.

In this aspect of the invention, an apparatus is provided for mixing at least two fluids with different thermal conductivity and comprising at least one device for measuring a mixing ratio k of the two fluids and a flow m of the mixed fluids, said device comprising a heating for generating, in said fluid, a region having non-homogeneous temperature, several sensors for determining at least two measured quantities t1, t2 depending on fluid temperatures in a range of influence of the heating, wherein the measured quantities are different functions $t1=f1(m, k)$ and $t2=f2(m, k)$ of the flow m and the mixing ratio k, and a processing circuit for determining the flow m and the mixing ratio k from the measured quantities t1, t2.

The device according to the invention can be designed such that it determines at least two measured quantities t1, t2, which depend on temperatures in the range of influence of the heating. These two measured quantities are chosen such that they are different functions $f1(v, k)$ and $f2(v, k)$, both depending on the flow m and a material parameter k. The material parameter k is a parameter depending on the thermal conductivity of the fluid. The two different functions $f1(m, k)$ and $f2(m, k)$ can be set equal to the measured quantities t1, t2, thereby forming a system of equations that allows the determination of the flow m and the material parameter k.

Due to this design, all measurements can be carried out with the same heating, while only two measured quantities have to be determined. If is, however, possible to determine a larger number of measured quantities, such as more than two temperature values at different points near the heating, if a higher accuracy is desired or more than one material parameter k is to be determined, e.g. the thermal conductivity as well as the heat capacity.

The device and method according to the invention can e.g. be used for measuring the composition of a fluid. It can e.g. be applied in an apparatus for mixing at least two fluids having different thermal conductivities. In this case, the parameter k is the mixing ratio of the fluids and can e.g. be used for monitoring or regulating the mixing ratio.

BRIEF DESCRIPTION OF THE DRAWINGS

The invention will be better understood and objects other than those set forth above will become apparent when consideration is given to the following detailed description thereof. Such description makes reference to the annexed drawings, wherein.

DETAILED DESCRIPTION OF THE INVENTION

Figure 1:
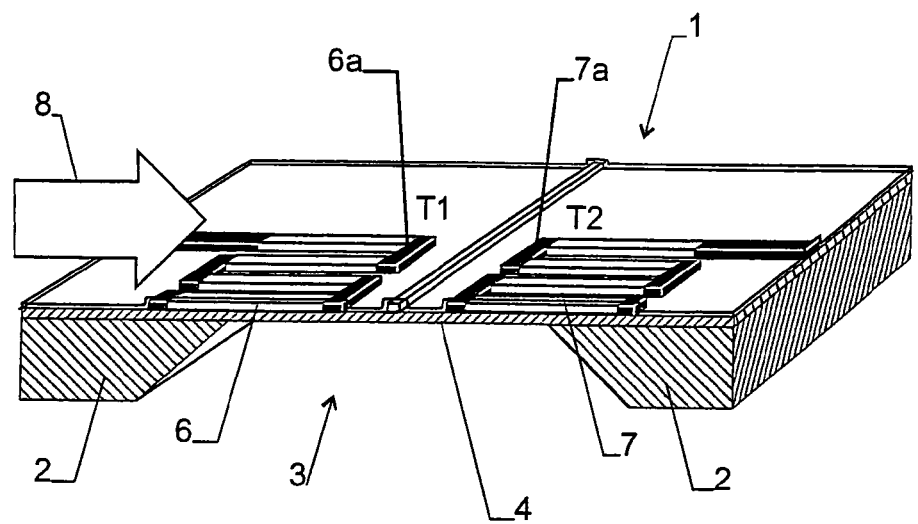
FIG. 1 is a partially sectional view of a region of the heating and the corresponding temperature detectors of an advantageous embodiment of the invention.
Figure 2:
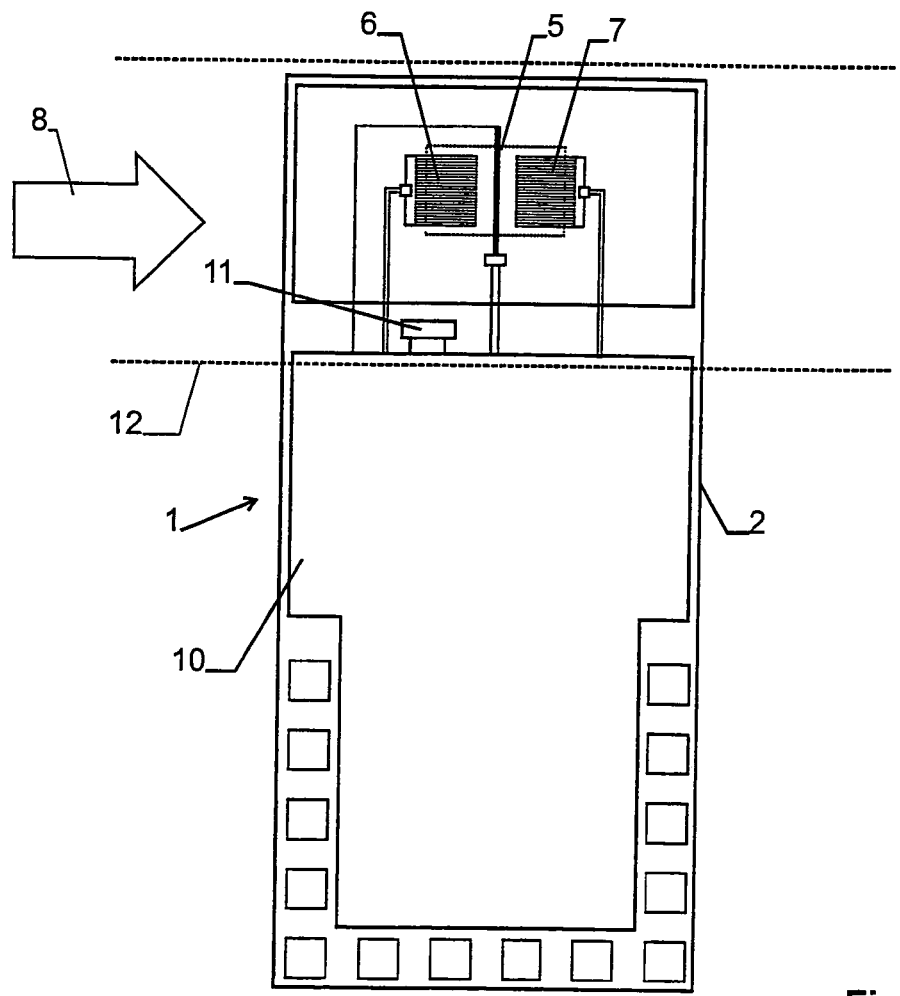
FIG. 2 is a top view of the sensor of FIG. 1.

In an advantageous embodiment of the invention, a sensor 1 such as shown in FIGS. 1 and 2 is used. The basic principle of operation of such a sensor is disclosed in WO 01/98736. As described in WO 01/98736, the sensor can be used for measuring the flow velocity m, or—more precisely—the mass flow, of a fluid, e.g. of a gas or a liquid.

The sensor is integrated on a silicon chip 2, in which an opening or recess 3 has been etched out. The opening or recess 3 is spanned by a membrane 4 made of a dielectric. A resistive heating 5 is arranged on membrane 4. Two thermopiles to be used as temperature detectors 6, 7 are arranged symmetrically to heating 5. The temperature detectors 6, 7 and heating 5 are arranged such in the flow direction 8 of the fluid that the fluid first passes first temperature detector 6, then heating 5 and finally second temperature detector 7.

Heating 5 generates an region of non-homogeneous temperature distribution in the fluid. This temperature distribution changes depending on the flow and on the thermal conductivity of the fluid. The two temperature detectors 6, 7 are arranged in the region of the non-homogeneous temperature distribution and can therefore register changes therein.

As can be seen from FIG. 2, a processing circuit 10 as well as a fluid temperature detector 11 are arranged on semiconductor chip 2. The function of processing circuit 10 is described below. Fluid temperature detector 11 serves to measure the temperature of the fluid and/or of the semiconductor chip 2, e.g. in order to convert the relative measurement of the thermopiles into absolute temperature values or, as described below, in order to correct the measured results. It is arranged outside the range of influence of heating 5.

At least the part of sensor 1 at the upper end of FIG. 2 with heating 5 and the temperature detectors 6, 7 and 11 is in thermal contact with a duct 12 holding the fluid. Sensor 1 can be arranged within duct 12 or at an outer wall thereof, wherein heating 5 and the temperature detectors 6, 7 and 11 must be in thermal contact with the fluid.

Two measured quantities t1 and t2 are determined by means of the temperature detectors 6 and 7. Measured quantity t1 corresponds to the difference between the temperatures T1 and T2 between the temperature detectors 6 and 7, i.e. the difference of temperature between the locations of the inner contact rows 6a, 7a of the temperature detectors. Measured quantity t2 corresponds to the temperature T2 at the location of inner contact row 7a of temperature detector 7 after heating 5, i.e. of the downstream temperature detector.

The measured quantities t1 and t2 depend in different manner from the mass flow m and the thermal conductivity $\lambda$ of the fluid, i.e. we have $$t1 = f1(m, k) \text{ and} \quad (1a)$$

$$t2 = f2(m, k), \quad (1b)$$

wherein k is the material parameter to be measured, i.e.

$$k = \lambda, \quad (2)$$

and f1, f2 are two different functions. The measurement of the measured quantities t1 and t2 defines the system of equations (1a), (1b) and allows the determination of the quantities m and k.

Advantageously, the function t1=f1(m, k) is determined by means of calibration measurements and stored in a table. For f2, we have, in approximation, $$T2 = t2 = f2(m, k) = g2(t1(m, k)) + h2(\lambda) \quad (3)$$
$$= [(c1 \cdot (1 - \exp(c2 \cdot t1(m, k))] + [c3 + c4 \cdot \lambda],$$

wherein the parameters c1 through c4 can be determined from calibration measurements.

In the above equations, the material parameter k to be measured is assumed to be the thermal conductivity $\lambda$ of the fluid. The material parameter k can, however, also be any other quantity that can be derived from the thermal conductivity of the fluid. If, for example, the fluid is a mixture of two components K1 and K2 with thermal conductivities $\lambda_1$ and $\lambda_2$, the system of equations (1a), (1b) allows the determination of the mixing ratio or of the amount k of the first component in the mixture. In that case, the thermal conductivity is approximately given by $$\lambda = \frac{y_1 \cdot \lambda_1}{y_1 + y_2 \cdot A_{12}} + \frac{y_2 \cdot \lambda_2}{y2 + y1 \cdot A_{21}} \quad (4)$$

mit $$A_{12} = \frac{\left(1 + \left(\frac{\lambda_1}{\lambda_2}\right)^{\frac{1}{2}} \cdot \left(\frac{y_1}{y_2}\right)^{\frac{1}{4}}\right)^2}{\left(8 \cdot \left(1 + \left(\frac{\lambda_1}{\lambda_2}\right)\right)\right)^{\frac{1}{2}}}$$

und $$A_{21} = \frac{\lambda_2}{\lambda_1} \cdot \frac{y_1}{y_2} \cdot A_{12}$$

wherein $y_1$ and $y_2$ are the molar masses of the two fluids.

By using (4) in equation (3), we again obtain a system of equations (a1), (1b), from which the material parameter k (or $y_1/y_2$) can be determined.

Figure 3:
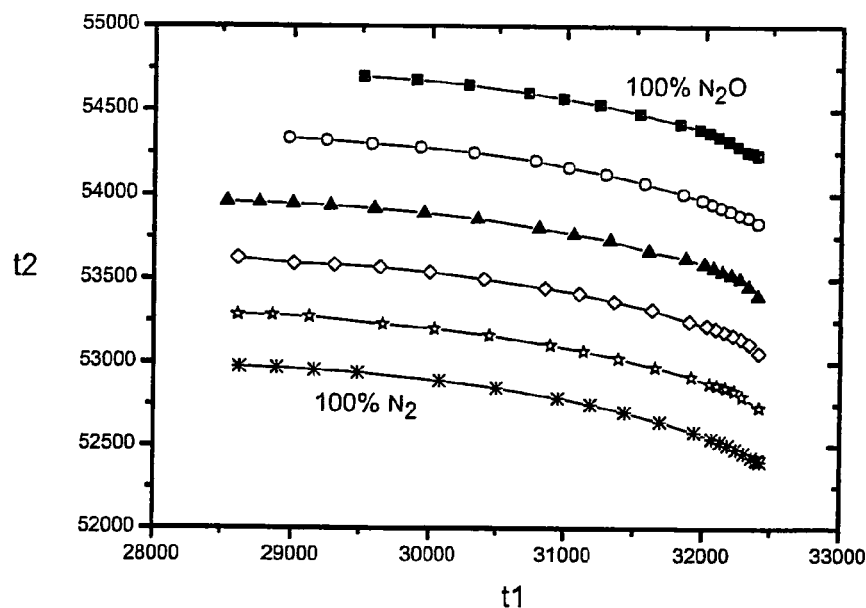
FIG. 3 shows typical measurements for gas mixtures with different mixing ratio (axis values in arbitrary units)

FIG. 3 illustrates the method in terms of a specific application. It shows the measured quantity t2 (the temperature at the temperature detector after the heating) as a function of the measured quantity t1 (temperature difference between the two temperature detectors) for measurements with a mixture of nitrogen (N) and laughing gas ($N_2O$), wherein the bottom most curve corresponds to pure nitrogen and the topmost curve to pure laughing gas. Each curve corresponds to measurements on a single mixture at several flow velocities.

As can be seen from FIG. 3, the knowledge of the values t1 and t2 allows an unambiguous selection of the corresponding curve and the corresponding mixing ratio or the corresponding thermal conductivity if a sufficient number of calibration curves as shown in FIG. 3 is available. In addition to this, the mass flow can be determined from the value t1 and/or the value t2, e.g. again using suitable calibration curves.

Instead of using a tabulated set of curves as shown in FIG. 3, it is also possible to solve the system of equations (1) directly. Corresponding numerical methods of computation are known to the person skilled in the art.

For even more accurate calculations, the temperature measured by fluid temperature detector 11 (FIG. 2) can be taken into account. As a rule, the functions f1 and f2 depend on the environmental temperature or the fluid temperature, which can be determined by fluid temperature detector 11, such that, if the temperature of detector 11 is taken into account, the accuracy of the determined flow m and/or the determined material parameter k can be improved.

The processing circuit for solving the systems of equation (1) and (3) can be partially or fully implemented on silicon chip 2. In particular, equation (1a) can be solved directly on the silicon chip.

The method described here can be generalized in various ways.

For example, instead of t1=T1−T2 and t2=T2, the quantities t1 and t2 can depend in other manner from the temperatures T1 and T2.

For example, measured quantity t2 can also correspond to temperature T2 of upstream temperature detector 6 even though a measurement with downstream temperature detector 7 generates more accurate results for most flow velocities.

Measured quantity t1 can also correspond to the temperature of upstream temperature detector 6 instead of corresponding to the temperature difference between the detectors. In this case, function f1 has to be modified accordingly.

It is also possible to place more than two temperature detectors into the region of influence of heating 5, the signals of which can be converted individually or in combination to further measured quantities t3, t4 etc. This makes the system of equations (1) correspondingly larger, which allows to determine further unknowns or to determine the mass flow and the material parameter k more accurately by means of the calculus of observations.

It is also possible to integrate a temperature detector directly into heating 5 by measuring its electric resistance. Further, it is possible to control the heating power in a closed loop in such a manner that the value of one of the measured quantities is kept constant, and to use the heating power instead of the controlled measured quantity for evaluation.

Figure 4:
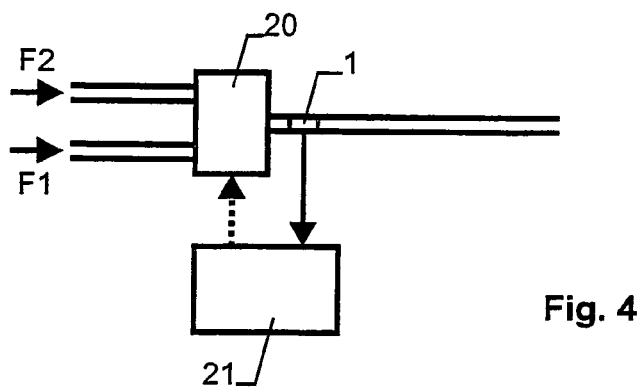
FIG. 4 shows an apparatus for mixing two fluids.

A preferred application of the invention is shown in FIG. 4, which shows an apparatus for measuring two fluids F1, F2. The apparatus comprises a mixing unit 20 for mixing the two fluids. The fluids have different thermal conductivity. A sensor 1 is arranged after mixing unit 20. Sensor 1 measures the mixing ratio between the two fluids using to the techniques described above. and feeds the result to a control unit 21. The mixing ratio measured in this way can be used for monitoring the mixing process and for issuing an alert if the mixing ratio passes above or below acceptable limits. It is also possible to control the mixing ratio in a closed loop if control unit 21 uses the measured mixing ratio for controlling mixer 20. Furthermore, not only the mixing ratio can be monitored or controlled, but also the flow rate of the mixture. In this case, the measured mixing ratio and the measured mass flow are used to control the mass flows before mixing unit 20.

Figure 5:
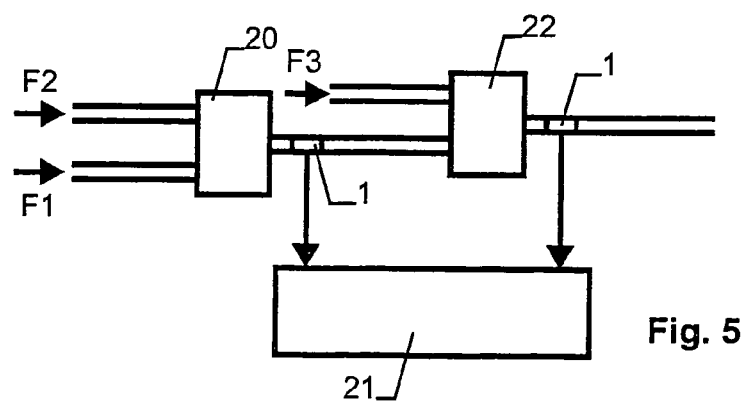
FIG. 5 shows an apparatus for mixing three fluids.

Sensor 1 even allows to measure the mixing ratio (and mass flows) or more than two fluids if they have sufficiently different thermal conductivities. For this purpose, the device of FIG. 5 can be used. Here, a first and a second fluid are fed to a first mixing unit 20. The first mixture generated in this way is fed to a second mixing unit 22, where it is mixed with a third fluid. A first sensor 1 is, as seen in the direction of flow, arranged between first mixing unit 20 and second mixing unit 22 and measures the mixing ratio between the first and the second fluid. A second sensor 1 is arranged after second mixing unit 22 and measures the mixing ratio between the first mixture and the third fluid, from which the mixing ratio of all fluids can be determined.

In an advantageous application, the device according to the invention can be used to monitor the composition of a mixture fed to a burner or a fuel cell. Measured quantity k can in that case be used for controlling the burner or the fuel cell, respectively. It can also be used for calculating the heating value, e.g. for calculating a fee for consumed fuel.

The device can also be used for monitoring a burner or a fuel cell. When used for fuel cells using hydrogen and oxygen, the device can e.g. be used for interrupting a fluid feed when the gas mixture achieves a critical mixing ratio at which there is a danger of explosions.

Devices and apparatus of the described type can also be used in anaesthetic equipment and artificial respiration equipment where the ratio between different gases, such as oxygen and laughing gas, has to be determined or controlled.

The described sensor can also be used for measuring the material parameter k of a fluid in rest.

While there are shown and described advantageous embodiments of the invention, it is to be distinctly understood that the invention is not limited thereto but may be otherwise variously embodied and practised within the scope of the following claims.

What is claimed is:

1. A device for measuring the flow m of a fluid of at least two substances and a mixing ratio k between the two substances of the fluid, said device comprising a heater for generating, in said fluid, a region having non-homogeneous temperature, several sensors for determining at least two measured quantities t1, t2 depending on fluid temperatures in a range of influence of the heater, wherein the measured quantities are different functions t1=f1(m, k) and t2=f2(m, k) of the flow m and the mixing ratio k, and a processing circuit for determining the flow m and the mixing ratio k from the measured quantities t1, t2.

2. The device of claim 1 wherein the sensors comprise a first and a second temperature detector, wherein the temperature detectors are arranged beside the heater and wherein the measured quantities t1 and t2 are derived from signals of the two temperature detectors.

3. The device of claim 2 wherein, as seen in a flow direction of the fluid, the first temperature detector is arranged before the heater and the second temperature detector is arranged after the heater.

4. The device of claim 3 wherein the measured quantity t2 corresponds to the fluid temperature at the second temperature detector.

5. The device of claim 2, wherein the measured quantity t1 corresponds to a difference between the fluid temperatures at the two temperature detectors.

6. The device of claim 5 wherein the material parameter k is the thermal conductivity of the fluid.

7. The device of claim 1 further comprising a fluid temperature detector arranged outside an area of influence of said heater, wherein the processing circuit is designed for using a signal from the fluid temperature detector when determining the material parameter k and/or the flow m.

8. The device of claim 1 further comprising a semiconductor chip, wherein the heater and the sensors are integrated on the semiconductor chip.

9. The device of claim 1 comprising exactly one heater.

10. An apparatus for mixing at least two fluids with different thermal conductivities, said apparatus comprising at least one device of claim 1.

11. An apparatus for mixing at least two fluids with different thermal conductivities and comprising at least one device for measuring a mixing ratio k of the two fluids and a flow m of the mixed fluids, said device comprising
  a heater for generating, in said fluid, a region having non-homogeneous temperature,
  several sensors arranged in said region for determining at least two measured quantities t1, t2 depending on fluid temperatures in a range of influence of the heater, wherein the measured quantities are different functions t1=f1(m, k) and t2=f2(m, k) of the flow m and the mixing ratio k, and
  a processing circuit for determining the flow m and the mixing ratio k from the measured quantities t1, t2.

12. The apparatus of claim 11 comprising a control unit for monitoring and/or regulating the mixing ratio.

13. An apparatus for mixing at least three fluids with different thermal conductivities and comprising at least two devices for measuring a mixing ratio k of the three fluids and a flow m of the mixed fluids, said apparatus comprising
  a first mixing unit for mixing a first and a second of the fluids into a first mixture and
  a second mixing unit for mixing the first mixture and a third of the fluids into a second mixture,
  wherein, as seen in a flow direction of the fluids, a first of said devices is arranged between the first and the second mixing unit and a second of said devices is arranged after the second mixing unit, and wherein each of said devices comprises
  a heater for generating, in said fluid, a region having non-homogeneous temperature,
  several sensors arranged in said region for determining at least two measured quantities t1, t2 depending on fluid temperatures in a range of influence of the heater, wherein the measured quantities are different functions t1=f1(m, k) and t2=f2(m, k) of the flow m and the mixing ratio k, and
  a processing means for determining the flow m and the mixing ratio k from the measured quantities t1, t2.

14. A method for measuring a flow m of a fluid and a material parameter k depending on a composition of the fluid, wherein the fluid is a mixture of a first and a second material and the material parameter k indicative of a mixing ratio between the materials, said method comprising the steps of
  bringing said fluid into contact with a heater for generating a region having non-homogeneous temperature in said fluid,
  determining at least two measured quantities t1, t2 depending on fluid temperatures in a range of influence of the heater, wherein the measured quantities are different functions t1=f1(m, k) and t2=f2(m, k) of the flow m and the material parameter k, and
  determining the flow m and the material parameter k from the measured quantities t1, t2.

15. The method of claim 14 further comprising the step of monitoring or regulating the mixing ratio using the material parameter k.

16. The method of claim 14 wherein the mixture is fed to a burner and the material parameter k is used for controlling or monitoring the burner.

17. The method of claim 14 wherein the mixture is fed to a fuel cell and the material parameter k is used for controlling or monitoring the fuel cell.

18. A device for measuring the flow m and at least one material parameter k of a fluid, wherein the material parameter k depends on a thermal conductivity of the fluid, said device comprising
  a heater for generating, in said fluid, a region having non-homogeneous temperature,
  a first and a second temperature detector arranged in said region for determining at least two measured quantities t1, t2 depending on fluid temperatures, wherein, as seen in a flow direction of the fluid, the first temperature detector is arranged before the heater and the second temperature detector is arranged after the heater,
  wherein the measured quantities are different functions t1=f1(m, k) and t2=f2(m, k) of the flow m and the material parameter k,
  wherein the measured quantity t1 corresponds to a difference between the fluid temperatures at the first and the second temperature detectors and
  wherein the measured quantity t2 corresponds to the fluid temperature at the second temperature detector,
  said device further comprising a processing circuit for determining the flow m and the material parameter k from the measured quantities t1, t2.

* * * * *